United States Patent [19]

Giersch et al.

[11] Patent Number: 4,929,599

[45] Date of Patent: May 29, 1990

[54] PERFUMING INGREDIENT

[75] Inventors: Wolfgang K. Giersch, Bernex; Karl-Heinrich Schulte-Elte, Onex, both of Switzerland

[73] Assignee: Firmenich SA, Geneva, Switzerland

[21] Appl. No.: 336,967

[22] Filed: Apr. 12, 1989

[30] Foreign Application Priority Data

Apr. 27, 1988 [CH] Switzerland ........................ 1575/88

[51] Int. Cl.[5] ........................ A61K 7/46

[52] U.S. Cl. ........................ 512/18; 560/256; 252/174.11

[58] Field of Search ........................ 512/18; 560/256; 252/174.11

[56] References Cited

U.S. PATENT DOCUMENTS

| | | | |
|---|---|---|---|
| 3,647,847 | 3/1972 | Curtis et al. | 512/18 |
| 4,100,110 | 7/1978 | Ansari et al. | 512/18 |
| 4,673,533 | 6/1987 | Boden et al. | 512/18 |

OTHER PUBLICATIONS

Reddy et al., Tetrahedron, vol. 42(16) pp. 4533-10 (1980).

*Primary Examiner*—James H. Reamer

*Attorney, Agent, or Firm*—Pennie & Edmonds

[57] ABSTRACT

The bicyclic ester represented by the formula

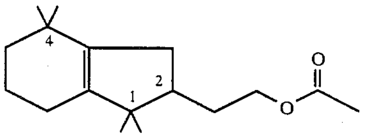

or 2-(2,3,4,5,6,7-hexahydro-1,1,4,4-tetramethyl-2(1H)-indenyl)-ethyl acetate, develops odor characters of the woody, slightly amber and musky type, and can therefore be advantageously used for the preparation of perfuming compositions or perfumes, and for perfuming products such as soaps, cosmetic preparations, detergents, fabric softeners or air deodorizers.

12 Claims, No Drawings

PERFUMING INGREDIENT

BRIEF SUMMARY OF THE INVENTION

The present invention relates to perfumery. It concerns more particularly a method for enhancing, improving or modifying the odor properties of a perfuming composition of perfumed product, which method comprises adding to said composition or product a fragrance effective amount of 2-(2,3,4,5,6,7-hexahydro-1,1,4,4-tetramethyl-2(1H)-indenyl)-ethyl acetate.

The invention also provides a perfuming composition containing as a perfuming ingredient 2-(2,3,4,5,6,7-hexahydro-1,1,4,4-tetramethyl-2(1H)-indenyl)-ethyl acetate.

A further object of the invention is to provide a perfumed product containing as a perfuming ingredient 2-(2,3,4,5,6,7-hexahydro-1,1,4,4-tetramethyl-2(1H)-indenyl)-ethyl acetate.

BACKGROUND OF THE INVENTION

The chemical structure of 2-(2,3,4,5,6,7-hexahydro-1,1,4,4-tetramethyl-2(1H)-indenyl)-ethyl acetate has been known for some time. The compound has in fact been described by R. T. Reddy and Y. R. Nayak in Tetrahedron 42, 4533 (1986). However, these authors only concerned themselves with examining the behavior of isolongifolene in the presence of a hydrogen halogenide, and separated the above-mentioned compound as an intermediate product without recognizing its intrinsic odor properties.

PREFERRED EMBODIMENTS OF THE INVENTION

It has now been discovered that 2-(2,3,4,5,6,7-hexahydro-1,1,4,4-tetramethyl-2(1H)-indenyl)-ethyl acetate possess very useful odor properties and that, as a result, it can be used advantageously as a perfuming ingredient for the preparation of perfume bases, perfuming compositions and perfumed products.

The odor properties of this compound are such that it can be used to develop notes of the woody, slightly amber type. This compound is also capable of imparting to the compositions to which it is added a very elegant musky note. These are very fine notes, perfectly convenient for the preparation of alcoholic perfumes or the reconstitution of natural oils, but which can equally be adapted for perfuming products such as shampoos, cosmetic preparations, body deodorants, soaps, powder or liquid detergents, fabric softeners or yet air deodorizers.

The bicyclic ester which is the object of the invention can be used alone in the above-mentioned products or, as is generally the case, in admixture with other perfuming ingredients, with solvents, diluting agents or carriers.

The proportions in which the compound of the invention can be used to achieve the desired perfuming effect vary within a wide range of values. The man skilled in the art is well aware that such concentrations can vary as a function of the specific fragrance effect desired and depends on the coingredients present in a given composition and on the nature of the products to be perfumed.

Thus, in many cases, concentrations of the order of 5–30% by weight, relative to the weight of the composition to which it is added, can be used. These values can of course be lower, for instance of the order of 0.1–0.5, or even 1%, when it is desired to perfume articles such as soaps, detergents or cosmetic preparations.

As coingredients, one can use any of the ingredients currently used in perfumery in admixture with the bicyclic ester of the invention, the usual criteria of physicochemical stability and odor compatibility being respected.

As previously mentioned, the chemical structure of 2-(2,3,4,5,6,7-hexahydro-1,1,4,4-tetramethyl-2(1H)-indenyl)-ethyl acetate is disclosed in the scientific literature. This compound can be obtained from isolongifolene by treatment with hydrobromic or hydroiodic acid, followed by esterification. The process for its preparation may be schematically represented as follows [see Tetrahedron 42, 4533 (1986)]:

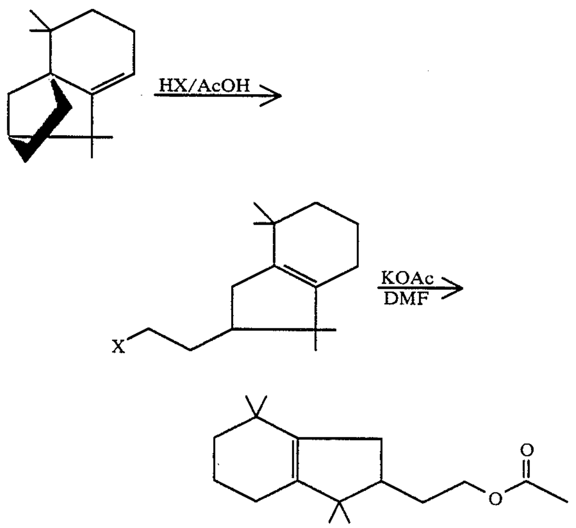

The invention will be illustrated in greater detail in the following non-restrictive examples.

EXAMPLE 1

Preparation of a perfumed detergent

A base composition consisting of a commercial powder detergent, with a neutral odor, was perfumed with 2-(2,3,4,5,6,7-hexahydro-1,1,4,4-tetramethyl-2(1H)-indenyl)-ethyl acetate, using 0.1 and 0.2% by weight of this compound relative to the weight of the base. As a result, a novel base was obtained possessing an odor character of the woody, balsamic and gently amber-musky type.

The thus obtained perfumed base composition was used for the general washing of linen, by means of an automatic washing machine at 60° C. After one cycle of washing and drying, the linen had a persistant and fresh character, and a fine, elegant woody, amber and musky odor.

EXAMPLE 2

Perfuming composition

A perfuming base composition of the "fougère" type was prepared by mixing the following ingredients (parts by weight):

| | |
|---|---|
| Benzyl salicylate | 180 |
| Bourbon geranium essential oil | 180 |
| Linalyl acetate | 160 |

-continued

| | |
|---|---|
| Lemon essential oil | 160 |
| Cyclosia (registered trademark) base(1) | 120 |
| Amyl salicylate | 120 |
| 10%* Ylang-ylang essential oil | 100 |
| Sweet orange essential oil | 90 |
| Lavender oil | 90 |
| 50%*(2) | 80 |
| 10%* Vanillin | 80 |
| Anisic aldehyde | 75 |
| Tarragon essential oil | 60 |
| Heliotropin | 60 |
| Linalol | 60 |
| Benzyl acetate | 50 |
| Patchouli essential oil | 45 |
| Oriental sandalwood essential oil | 45 |
| 50%* Oakmoss absolute | 40 |
| Phenylethanol | 40 |
| Citronellol | 25 |
| Bourbon vetyver essential oil | 20 |
| Coumarin | 10 |
| Methylnaphthylacetone | 10 |
| Total | 1900 |

*in diethyl phathalate
(1)Firmenich SA: hydroxycitronellal
(2)Schiff base hydroxycitronellal/methyl anthranilate The addition of 30 g of 2-(2,3,4,5,6,7-hexahydro-1,1,4,4-tetramethyl-2(1H)-indenyl)-ethyl acetate to 190 g of the base composition thus prepared resulted in a novel composition whose overall odor character was richer, with a musky and ambrette side. The woody note of the base composition was also strengthened, resulting in increased volume.

EXAMPLE 3

Perfuming composition

A perfuming base composition for a masculine line was prepared as follows (parts by weight):

| | |
|---|---|
| p-tert-Butyl-cyclohexyl acetate | 200 |
| 10%* Oakmoss absolute | 180 |
| Synthetic bergamot oil | 140 |
| alpha-Hexylcinnamic aldehyde | 80 |
| Iralia (registered trademark)(1) (4) | 60 |
| Hedione (registered trademark)(2) (4) | 20 |
| Resinoid galbanum | 20 |
| Lavandin absolute | 20 |
| Dihydromyrcenol | 20 |
| Synthetic neroli oil | 20 |
| Synthetic basil oil | 20 |
| 10%* Methyl-nonyl aldehyde | 20 |
| Resinoid olibanum | 20 |
| 20%* Pine absolute | 10 |
| Synthetic angelica root oil | 10 |
| Eugenol | 10 |
| 50%* Resinoid labdanum | 10 |
| Rosemary essential oil | 10 |
| Cypress essential oil | 10 |
| Mayol (registered trademark)(3) (4) | 10 |
| Isoeugenol | 5 |
| 50%* Resinoid Benjoin Siam | 5 |
| Total | 900 |

*in diethyl phthalate
(1)alpha-methylionone
(2)methyl dihydrojasmonate
(3)p-isopropyl-cyclohexylmethanol
(4)origin: Firmenich SA, Geneva The addition of 10 g of 2-(2,3,4,5,6,7-hexahydro-1,1,4,4-tetramethyl-2(1H)-indenyl)-ethyl acetate to 90 g of this woody, aromatic, herbaceous base composition resulted in a novel composition whose odor character was much more elegant and round than that of the said base composition. In particular, the citrus note harmonized better. Furthermore, the new composition had a musk-ambrette odor.

What we claim is:

1. A method for enhancing, improving or modifying the odor properties of a perfuming composition or perfumed product, which method comprises adding to said composition or product a fragrance effective amount of 2-(2,3,4,5,6,7-hexahydro-1,1,4,4-tetramethyl-2(1H)-indenyl)-ethyl acetate.

2. A perfuming composition comprising a perfuming ingredient of 2-(2,3,4,5,6,7-hexahydro-1,1,4,4-tetramethyl-2(1H)-indenyl)-ethyl acetate in admixture with a perfume coingredient.

3. A perfumed product comprising a base composition and, as a perfuming ingredient, a fragrance effective amount of 2-(2,3,4,5,6,7-hexahydro-1,1,4,4-tetramethyl-2(1H)-indenyl)-ethyl acetate.

4. The perfumed product according to claim 3, wherein the base composition is a detergent article comprising a soap or a liquid or powder detergent.

5. The method of claim 1 wherein the perfuming ingredient is present in an amount of between 0.1 to 30% by weight of the composition or product.

6. The method of claim 1 wherein a perfuming coingredient is present in admixture with said perfuming ingredient.

7. The composition of claim 2 wherein the perfuming ingredient is present in an amount of between 0.1 to 30% by weight of the composition.

8. The product of claim 3 wherein a perfuming coingredient is present in admixture with said perfuming ingredient.

9. The product of claim 3 wherein the perfuming ingredient is present in an amount of between 0.1 to 30% by weight of the product.

10. The product of claim 4 wherein a perfuming coingredient is present in admixture with said perfuming ingredient.

11. The product of claim 4 wherein the perfuming ingredient is present in an amount of between 0.1 to 30% by weight of the product.

12. The product of claim 11 wherein a perfuming coingredient is present in admixture with said perfuming ingredient.

* * * * *